United States Patent
Bos et al.

(10) Patent No.: US 8,049,044 B2
(45) Date of Patent: Nov. 1, 2011

(54) REMEDIATION PROCESS AND APPARATUS

(75) Inventors: Alouisius Nicolaas Rene Bos, Amsterdam (NL); Dominicus Maria Rekers, Amsterdam (NL); Arthur Willibrordus Titus Rots, Amsterdam (NL)

(73) Assignee: Shell Oil Company, Houston, TX (US)

( * ) Notice: Subject to any disclaimer, the term of this patent is extended or adjusted under 35 U.S.C. 154(b) by 1587 days.

(21) Appl. No.: 10/740,048

(22) Filed: Dec. 18, 2003

(65) Prior Publication Data
US 2004/0175316 A1   Sep. 9, 2004

(30) Foreign Application Priority Data
Dec. 23, 2002 (EP) .................................... 02258881

(51) Int. Cl.
*C07C 27/00* (2006.01)
*B01D 19/00* (2006.01)
(52) U.S. Cl. ............. 568/858; 568/867; 95/160; 95/162
(58) Field of Classification Search .................. 568/867, 568/858; 95/160, 162
See application file for complete search history.

(56) References Cited

U.S. PATENT DOCUMENTS

| | | | |
|---|---|---|---|
| 3,867,113 A | 2/1975 | Foster et al. .................... 55/44 |
| 4,397,660 A * | 8/1983 | Van der Pas-Toornstra .... 95/162 |
| 4,508,927 A * | 4/1985 | Bhise et al. .................... 568/858 |
| 4,831,196 A | 5/1989 | Buonicore et al. ............ 568/867 |
| 5,106,458 A | 4/1992 | Meyer et al. .................... 203/38 |
| 5,763,691 A * | 6/1998 | Kawabe et al. ............... 568/867 |

FOREIGN PATENT DOCUMENTS

| | | |
|---|---|---|
| DE | 198 43 721 | 9/1998 |
| EP | 776890 | 6/1997 |
| GB | 498119 | 1/1939 |
| WO | WO 84/00748 | 3/1984 |

OTHER PUBLICATIONS

International Search Report, dated Apr. 23, 2004.
PCT International Preliminary Examination Report, International Application No. PCT/EP 03/51095 filed Dec. 23. 2003.

* cited by examiner

*Primary Examiner* — Andrew D Kosar
*Assistant Examiner* — Raymond Covington

(57) ABSTRACT

The invention relates to a process for remediation of a fluid contaminated with alkylene oxide, involving contacting the contaminated fluid with an aqueous absorbent to yield a fat absorbent having absorbed fluid, conferring intimate contact of fat absorbent and alkylene oxide and conversion of alkylene oxide; and, an apparatus for remediation of the fluid which has a converter having inlet means connected to the outlet of a fluid absorber for contacting fluid and aqueous absorbent, a holding unit having a volume V for the fat absorbent, and outlet means connected to the inlet of a fluid desorber.

21 Claims, 7 Drawing Sheets

Block scheme of the EO/EG process

Figure 1    Block scheme of the EO/EG process
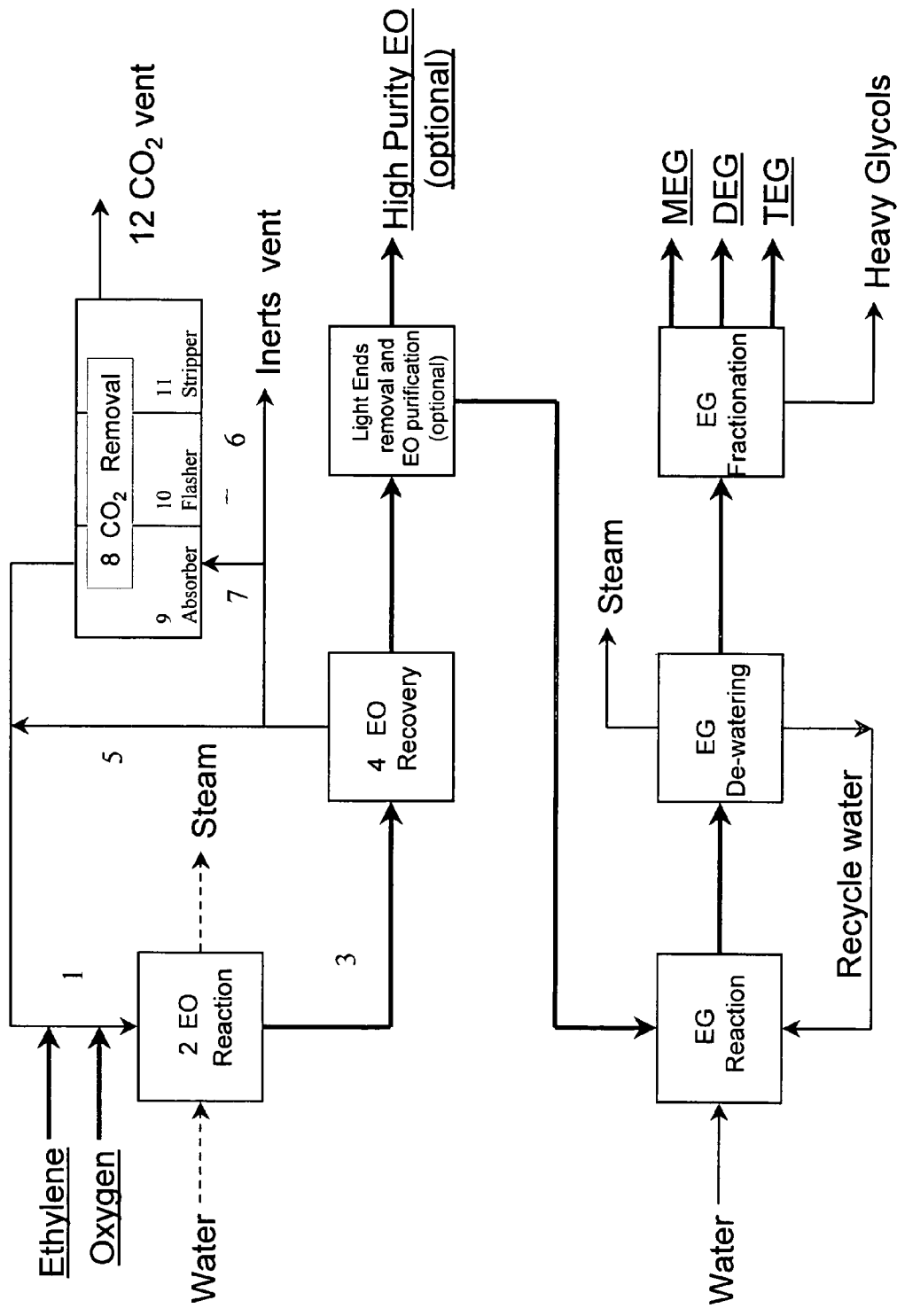

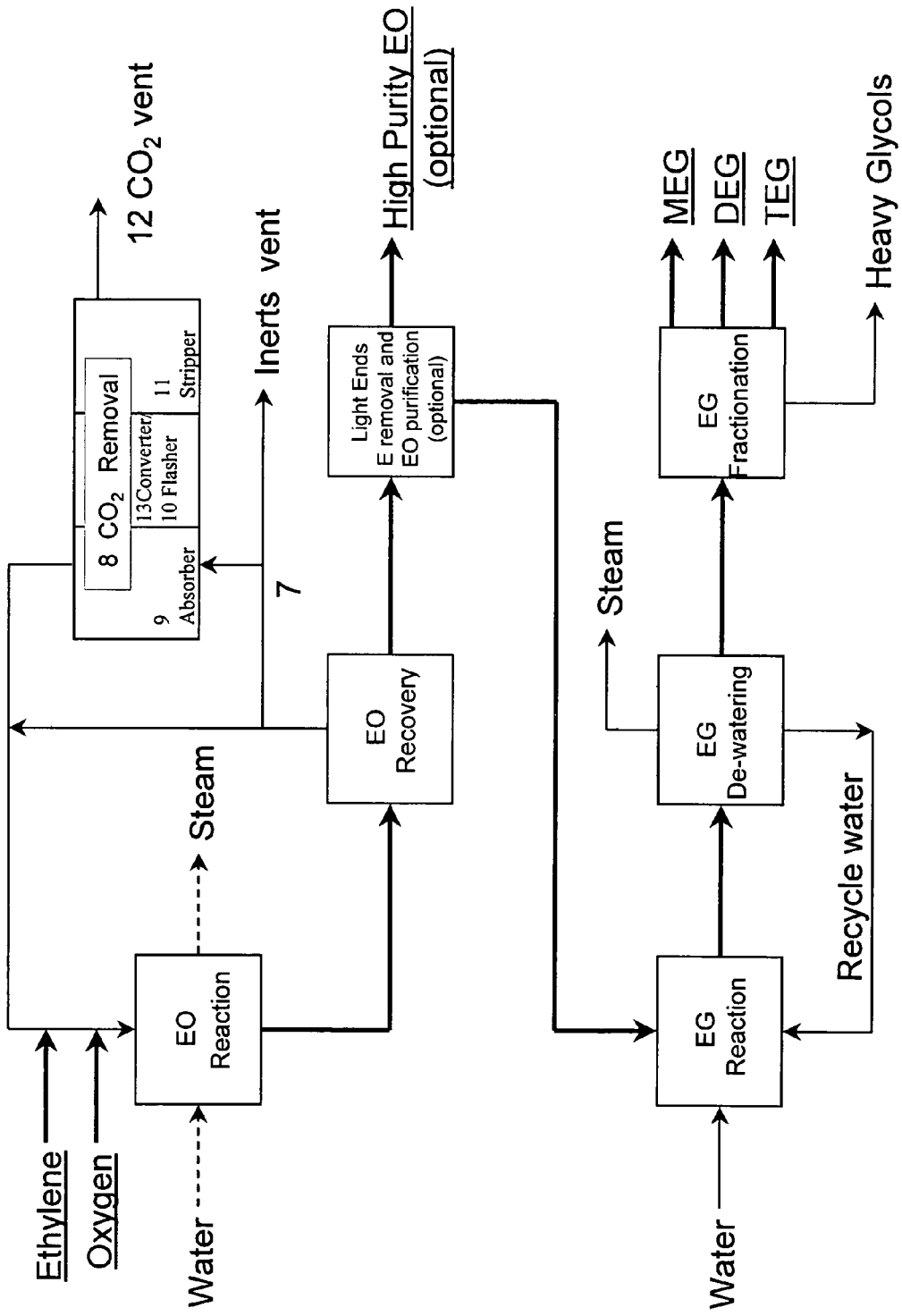
Figure 2 Block scheme of the modified EO/EG process

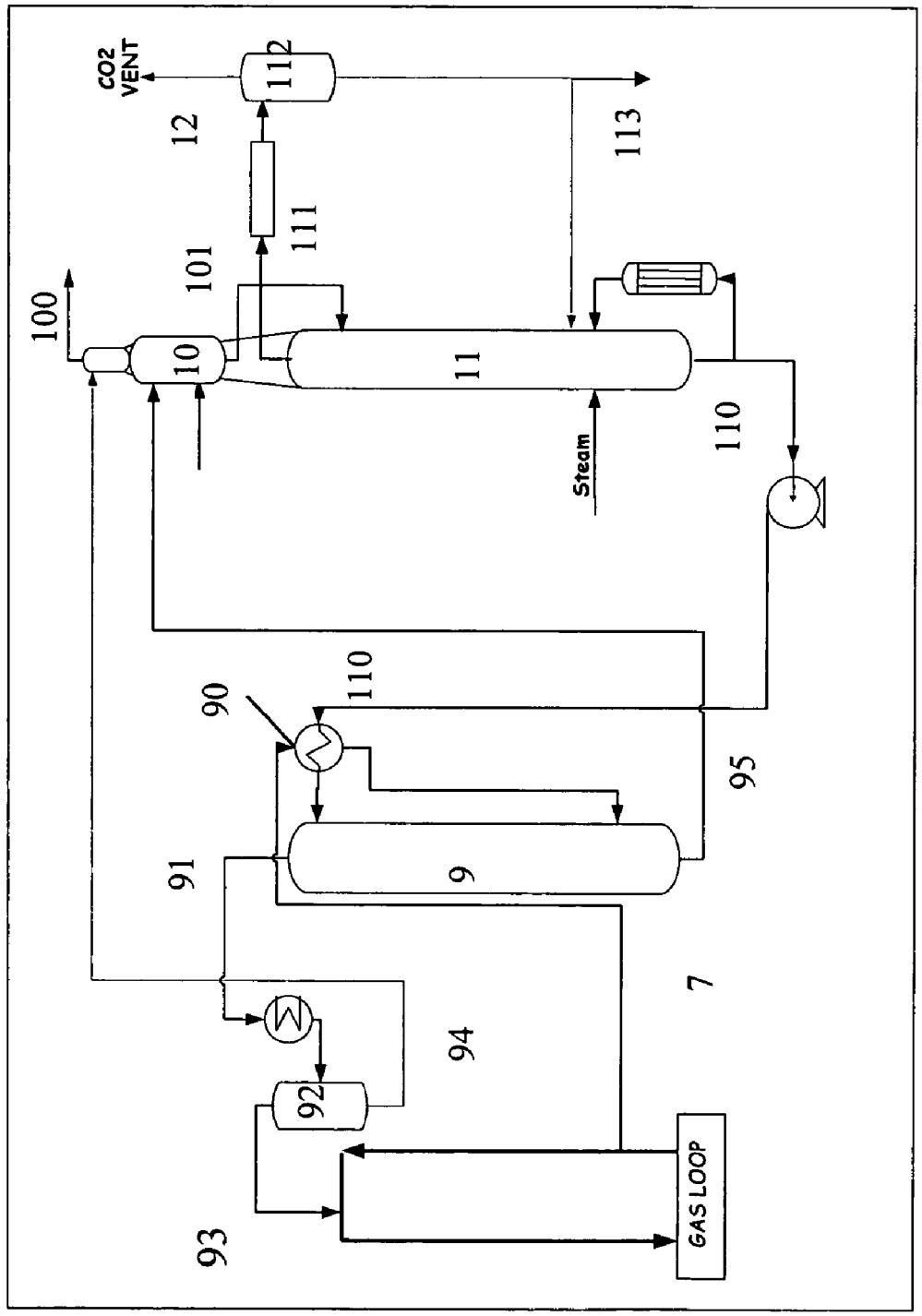
Figure 3 CO2 Removal Unit - conventional

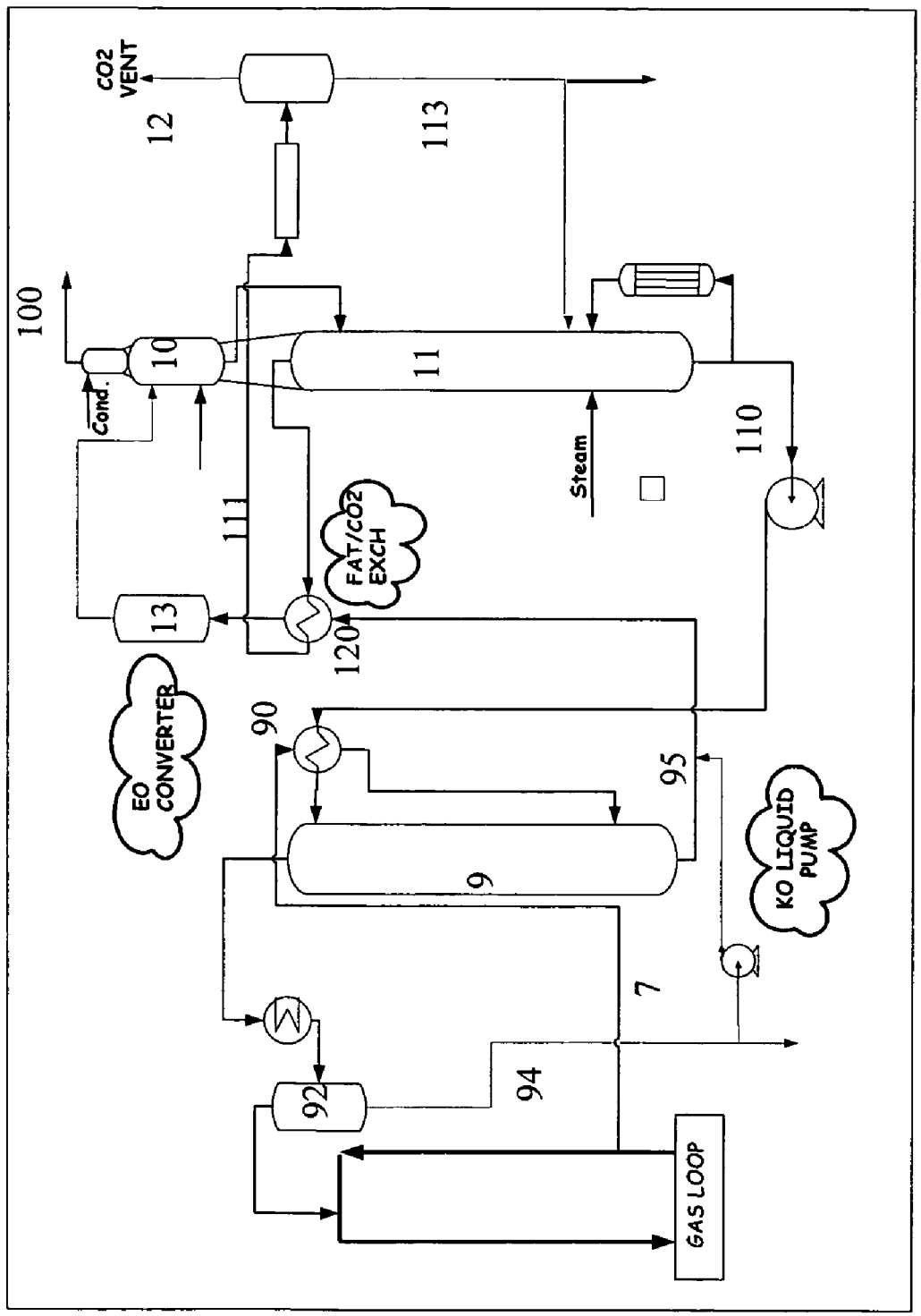
Figure 4 CO$_2$ Removal Unit - with EO converter

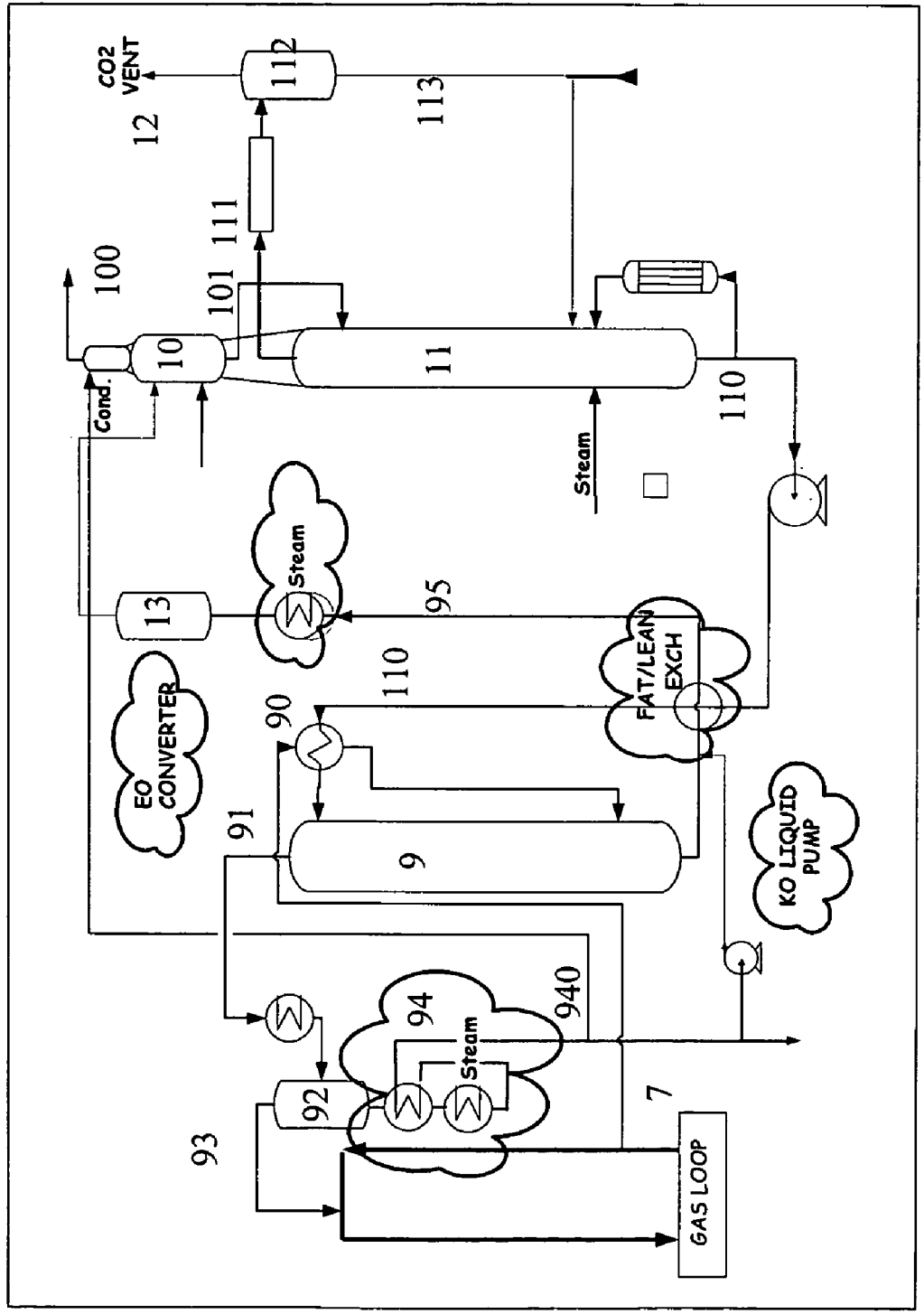
Figure 5 CO₂ Removal Unit - with EO converter - alternative

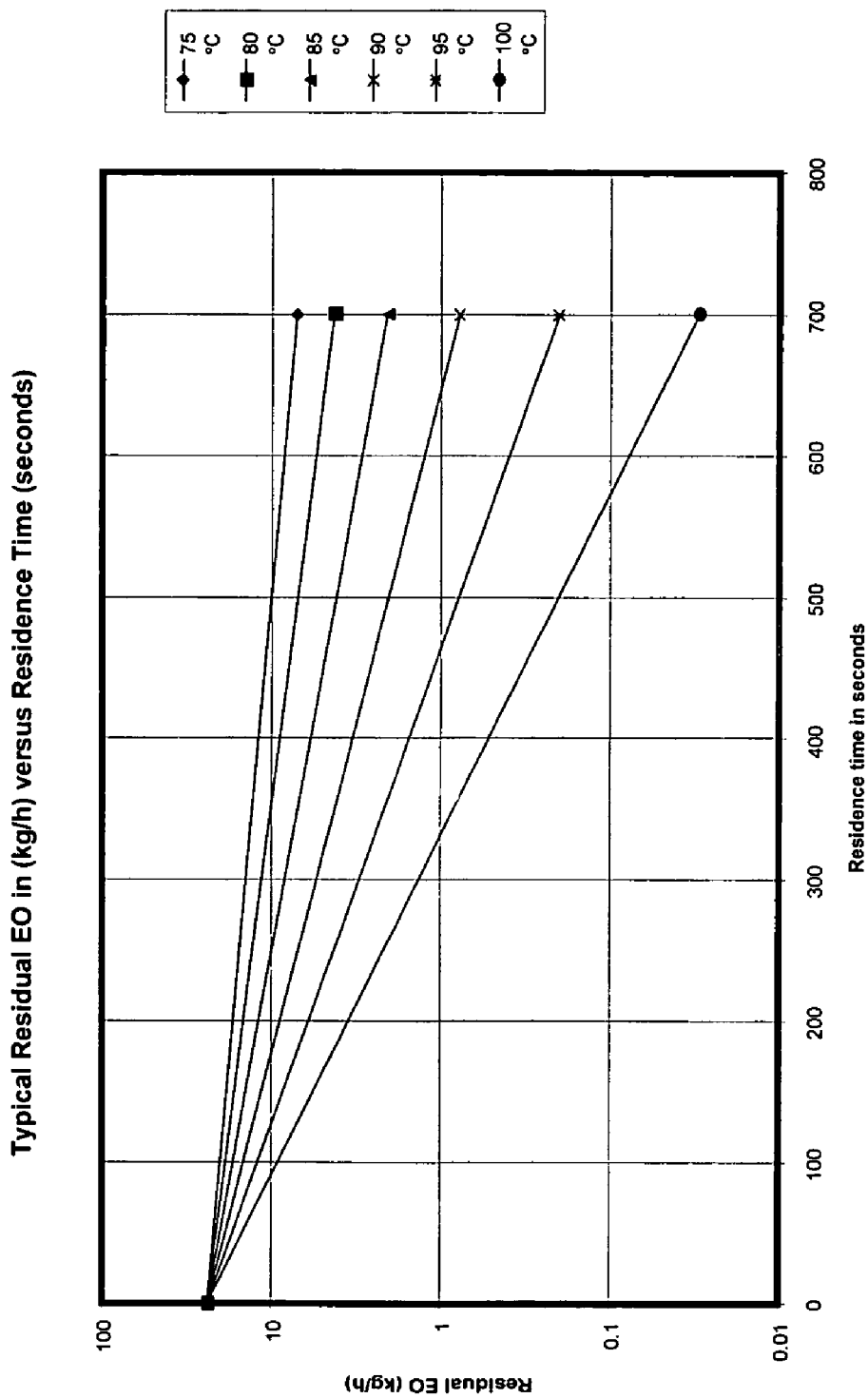
Figure 6 – Typical Residual EO versus Residence Time

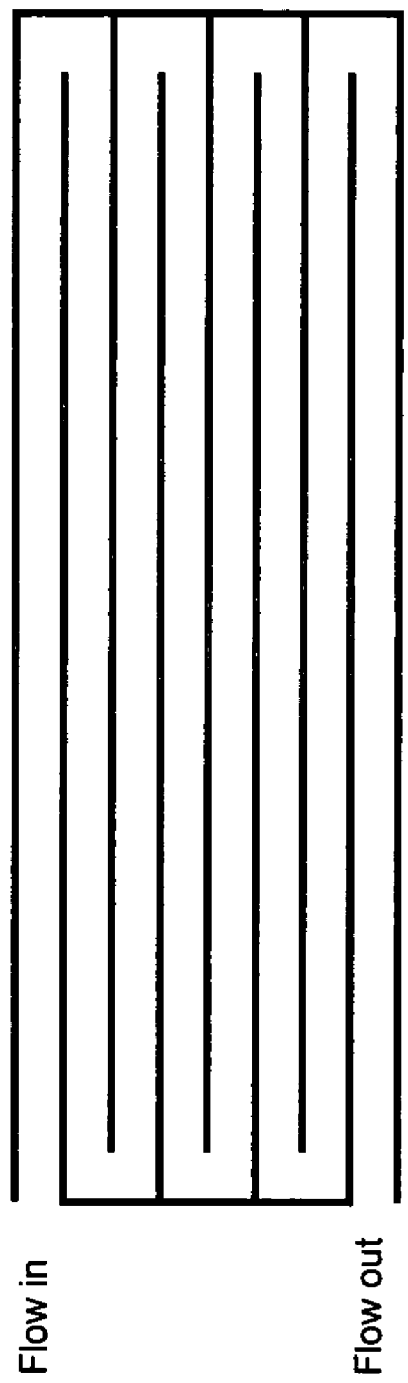
Figure 7 – Schematic drawing of a variant Holding Unit

REMEDIATION PROCESS AND APPARATUS

FIELD OF THE INVENTION

The present invention relates to a process for remediating a fluid containing minor amounts of ethylene oxide, and an apparatus therefore and the use thereof, in particular, in remediating a $CO_2$ vent stream from an ethylene oxide (EO) process.

BACKGROUND OF THE INVENTION

Ethylene oxide is a substantial item of chemical commerce having utility both as a sterilization agent and as a fumigant, but primarily as a starting material in the manufacture of a diverse array of products such as anti-freeze, cosmetics, lubricants, plastics and surfactants. The major process for manufacture of ethylene oxide is by the silver-catalyzed oxidation of ethylene. Typically, the stream exiting the reactor comprises small quantities of ethylene oxide (for example 0.5 to 5 mol %) together with large amounts of residual gases including unconverted ethylene and oxygen as well as appreciable quantities of carbon dioxide, low molecular weight hydrocarbons and inert gases such as nitrogen. Customarily, the ethylene oxide product is recovered from the residual gases by absorption in water followed by processing of the ethylene oxide-fat absorbent in a variety of ways including fractionation, scrubbing, stripping and the like.

An ethylene oxide plant may also be the site of production of monoethylene glycol derived by hydration of the product ethylene oxide. In such a plant, the product ethylene oxide, having been isolated by water absorption, is then typically hydrated in a separate reactor.

Variations of this process have been proposed in the past. GB-A-498,119 for example is an early proposal where the hydration may be performed thermally or, preferably, using an acidic catalyst which is added to the water absorbent. The glycol forms on heating the absorbent solution after the ethylene oxide is absorbed and the resulting solution is recycled as liquid absorbent until the glycol content is relatively high and is recovered.

EP-A2-776890 proposes another variant where ethylene oxide absorbed in a solution containing ethylene carbonate and ethylene glycol is reacted with carbon dioxide to the carbonate form and hydrolyzed with a separate catalyst. The Example shows that treatment of an ethylene oxidation product stream, containing 3 mol % ethylene oxide, left 100 ppm in the residual gases, following the particular absorption step and conditions used.

DE-A1-19843721 uses ethylene oxide wash water as absorbent prior to the hydration step. The Example shows absorption in wash-water of ethylene oxide from a gas mixture containing 2.7 mol % ethylene oxide, leaving 10 ppm ethylene oxide to be lost in the residual gases.

The residual gases that remain after recovery of the bulk ethylene oxide product are recycled to the ethylene oxidation reactor. Customarily, a small bleed stream is withdrawn from the recycled gases to prevent build-up of impurities such as argon, ethane or nitrogen in the recycle gas loop. A side stream, being part or all of the recycle gas, is usually scrubbed with an aqueous carbon dioxide ($CO_2$) absorbent for removal of excess $CO_2$ which is subsequently stripped from the absorbent and typically is vented, or if desired, recovered for use or sale as a by-product.

A problem arises, particularly in manufacturing plants of large capacity, in that, during scrubbing of the recycle gas side stream, small amounts of hydrocarbon are dissolved and/or entrained in the $CO_2$ absorbent and ultimately vented with the carbon dioxide.

U.S. Pat. No. 3,867,113 discloses a process improvement which is now conventional in EO processes, whereby the $CO_2$-fat absorbent obtained by contacting a sidestream from the recycle stream with a $CO_2$ absorbent is flashed to form a hydrocarbon-containing vapor stream and a hydrocarbon-lean fat absorbent, and the fat absorbent is stripped to produce a $CO_2$ stream substantially free of hydrocarbon which is suitable for venting, or use.

Nevertheless, in conventional EO plants, despite flashing the fat absorbate, a small amount of residual EO remains in the vent gas from the $CO_2$ stripper. In order to keep vented EO as small as possible for environmental reasons, the vent gas can therefore, conventionally, be subject to incineration. Such incineration can, for example, occur within a catalytic incinerator whereby one or more catalyst beds are heated to high temperatures (in ranges from approximately 300° C. to 800° C.) and various heat exchange mechanisms are incorporated to minimize energy loss and improve efficiency. This, therefore, presents a convenient solution which is effective in operation and, as an "end-of-pipe" process, requires minimal alteration to the existing process line up.

Being operated at high temperatures and requiring the need for catalyst will, however, inevitably mean periods of time in which the incinerator cannot function due to the need for maintenance, repair, replacement of catalyst, etc. Where environmental contamination is measured on an average basis, say as EO vented per week, such incinerator-downtimes are negligible, but increasingly, environmental concerns require constant monitoring of EO venting with hourly measurement of contamination, and this means that the conventional incinerator system may not comply with environmental regulations all of the time.

There is therefore a need to provide for an effective reduction of EO in $CO_2$ vent gas from an EO plant, with or without the use of additional incineration, in which reduction is constantly maintained.

The concentration of EO in vent gas is moreover dependent on a number of factors, including the percent of recycle stream which is treated as a sidestream, and the operating conditions of the $CO_2$ absorber and EO absorber. A further need is, therefore, to provide a system for independent control of EO in $CO_2$ vent gas from an EO plant, whereby the level of carbon dioxide to be vented can be varied without compromising the reduction in EO emission.

SUMMARY OF THE INVENTION

The invention provides a process for remediation of a fluid contaminated with up to 1000 ppmv of alkylene oxide comprising contacting the contaminated fluid with an aqueous absorbent to confer intimate contact of absorbent and alkylene oxide and conversion of alkylene oxide.

In a further aspect of the invention there is provided a method for calculating a required residence time of fat absorbent in a process for remediation of fluid as herein defined, from the moment of fluid absorption to the moment of fluid stripping to generate lean absorbent, in manner to convert a desired amount of ethylene oxide as herein defined.

In a further aspect of the invention there is provided an apparatus for remediation of fluid as herein defined contaminated with an amount of alkylene oxide, wherein the apparatus comprises a converter having inlet means connected to the outlet of a fluid absorber for contacting fluid and aqueous absorbent, a holding unit having a volume V for the fat absorbent, and outlet means connected to the inlet of a fluid desorber.

BRIEF DESCRIPTION OF THE DRAWINGS

FIG. 1—the EO/EG process illustrated as a block scheme.
FIG. 2—the $CO_2$ removal section in a modified EO/EG process incorporating the process of the invention is illustrated as a block scheme.
FIG. 3—the EO/EG process illustrated as a process sketch.
FIG. 4—a preferred modification of the invention.
FIG. 5—the $CO_2$ removal section in a modified EO/EG process incorporating the process of the invention is illustrated as a process sketch.
FIG. 6—typical residual EO versus residence time
FIG. 7—schematic drawing of a variant holding unit

DETAILED DESCRIPTION OF THE INVENTION

We have now surprisingly found that chemicals present during $CO_2$ absorption in the carbonate section may also be highly effective in catalyzing the reaction of EO to glycol, under certain specific conditions. Even more surprisingly, we have found that these specific conditions may be conveniently provided without major alteration of an existing EO plant, or without major design changes in a new plant, and this is of course of major importance as significant changes would affect other control and emission measures.

While the combination of absorption of olefins and hydration to glycol is utilized extensively, e.g. in the combined production of ethylene oxide and monoethylene glycol as noted above, use of absorption and hydration has never previously been proposed to remove, for example, the very low levels of ethylene oxide that occur as a contaminant in $CO_2$-rich vent gas. Moreover, the removal can be continuously and effectively achieved in preferred embodiments without the addition of any other additive than the aqueous absorbent conventionally utilized in a commercial EO process for $CO_2$ absorption. This is the more surprising since the contaminant levels of EO remain following an extensive absorption process in the conventional production of EO and it would normally be expected that a different or more rigorous treatment, such as the incineration of previous proposals, would be necessary to remove the low levels remaining.

Contamination of gas streams by alkylene oxides may also occur in other commercial operations. However the most preferred application of the process, control system and apparatus of the present invention is the reduction of EO in $CO_2$ vent gas, and throughout the specification the present invention will most frequently be described with reference to this use.

Preferably, the process of the invention comprises contacting the contaminated fluid with an aqueous absorbent to yield a fat absorbent having absorbed fluid, conferring intimate contact of fat absorbent and alkylene oxide and conversion of alkylene oxide. Absorption may be of all or part of the contaminated fluid which is contacted with absorbent, and is typically of part of the contaminated fluid.

Preferably, alkylene oxide is converted to glycol in the process of the invention. In a particular advantage glycol can be separated in subsequent stages as a liquid condensate, yielding remediated fluid.

Reference herein to a fluid is to a fluid stream, reservoir or the like and is preferably a fluid stream. Fluid may be of gas or liquid form, such as a gas, vapor or condensed vapor, or other liquid. Preferably, the fluid comprises a gas stream comprising an amount of alkylene oxide. Alternatively or additionally, the fluid may comprise condensed vapor, such as condensed steam, comprising an amount of alkylene oxide. Preferably, the fluid comprises a $CO_2$ containing stream, especially a $CO_2$-rich stream, contaminated with ethylene oxide (EO), more preferably from the partial oxidation of ethylene to ethylene oxide by the EO process in an EO unit in which the $CO_2$ is intended for venting. A $CO_2$-rich stream suitably contains up to 10 mol %, for example in the range of from 0.1 mol % to 6 mol %, preferably 0.5 mol % to 6 mol %. Suitable examples are from 3 mol % to 6 mol % $CO_2$, but also 0.5 mol % to 3 mol %.

In a particular embodiment, the contaminated fluid is absorbed as hereinbefore defined and provides a suitable medium for combining contaminated fluid and converting alkylene oxide from other sources. Preferably, therefore, the process of the invention comprises contacting fluid and absorbent as hereinbefore defined and simultaneously or subsequently additionally combining one or more additional alkylene oxide contaminated fluids for conversion of alkylene oxide as hereinbefore defined. Such additional streams may for example include condensed steam which has been used for scrubbing or the like, such as absorber overhead gas knockout, absorbent which has been used to absorb alkylene oxide from other streams and the like.

Combining fluids is preferably carried out with mixing, more preferably to provide a uniform fat absorbent composition.

The process is suitable for converting alkylene oxide present in any amount up to 1000 ppmv, for example in the range of from 0.1 ppmv up to 1000 ppmv, preferably 0.1 ppmv to 500 ppmv. It is of particular significance that the process is able to convert residual amounts of ethylene oxide of, or in excess of, 0.1 ppmv up to 40 ppmv.

The process may be operated at any desired conversion. Conditions may be chosen to give a desired conversion depending on the level of alkylene oxide present.

It is a particular advantage that the process is characterized by a very high conversion whereby the absorbed fluid may be substantially completely remediated by the process of the invention, preferably the process is characterized by conversion substantially greater than or equal to 50%, more preferably substantially greater than or equal to 80%, for example from 88% to substantially complete conversion, preferably from 90% to 99.9999%, more preferably from 95% to 99.999%. This enables reduction of alkylene oxide to below 1 ppmv and especially to below 0.1 ppmv.

Suitably, the process comprises, in a further stage, desorbing the absorbed fluid, thereby generating a lean absorbent stream, separating the alkylene oxide conversion product and recycling the lean absorbent. Preferably, the process comprises separating any volatile hydrocarbons by flashing the fat absorbent prior to desorbing the absorbed fluid by stripping. Preferably, the absorbed fluid is a gas and the process comprises separating the alkylene oxide conversion product by phase separation by, for example, condensation or knockout, to form condensed liquids and a remediated fluid which is substantially free of alkylene oxide, preferably having a maximum residual alkylene oxide level of 1 ppmv or less, more preferably of 0.1 ppmv or especially less than 0.1 ppmv.

Aqueous absorbent may be selected from any aqueous solution which is not deleterious to catalysts or other components, if any, present in other stages of the process. Preferably, the absorbent is selected from alkali metal carbonates such as sodium (bi) carbonate, potassium (bi) carbonate; water; methyl alcohol; acetone; and solvents such as propylene carbonates or ethylene carbonates; and the like; and mixtures thereof with other absorbents or fillers. More preferably, the absorbent is a $CO_2$ absorbent. The absorbent is especially an alkali metal carbonate. In a typical absorption system the lean absorbent solution may contain for example $K_2CO_3$ and $KHCO_3$ in a ratio of about 70:30. When $CO_2$—containing gas is passed through the absorber, reaction of $CO_2$ with the carbonate solution results in conversion of up to about 90% $K_2CO_3$, leaving about 10% $KHCO_3$. The absorbent may contain activators and the like for improved absorption. Known and preferred activators include potassium or sodium salts of metal oxides such as vanadate, chromate and borate and mixtures thereof. Preferably the absorbent is selected from commercially available $CO_2$ absorbents such as Catacarb or Benfield solutions. Benfield absorbents are disclosed for example in GB 1415036, U.S. Pat. Nos. 3,863,003, 3,907,969, the contents of which are incorporated herein by reference.

The process is suitably carried out under conditions conducive to conversion of alkylene oxide. Conditions conducive to conversion of alkylene oxide include conditions selected from low or high pH, presence of activators, elevated temperature, extended residence time, and the like.

For example, the fluid may be acidic, alkaline or neutral, and/or may form an acidic, alkaline or neutral fat absorbent. For example, the fat absorbent may be acidic or alkaline and have a pH<4 or pH>9. More preferably, the fat absorbent is neutral to alkaline having a pH in the range of from 7 to 11, most preferably 9 to 11, and especially 10 to 11.

The fat absorbent may be activated by the presence of an amount of activator selected from substances which promote or catalyse the conversion of alkylene oxide. Activator is preferably derived from an available process component, but may be added to the absorbent or the fluid. It is possible that $CO_2$ present in a fluid to be remediated, for example, may promote conversion of alkylene oxide by virtue of its acidity in solution or by virtue of an activating effect.

The conversion of ethylene oxide to glycol has been observed to take place with high conversion by a modification downstream of the $CO_2$ absorption stage in the EO process, in which $CO_2$, absorbent, activators and water are present as fat absorbent, the modification comprising intentionally increasing fat absorbent residence time beyond that required for conventional absorption and separation. Without being limited to this theory, it is thought that the conversion of alkylene oxide to glycol may be facilitated by one or a number of conditions selected from the presence of activators, acid, alkali, and/or other catalyst and water both for activation and being consumed in the conversion, and conditions such as elevated temperature, extended residence time and the like. The rate of conversion depends on conditions of temperature, presence of activators and the like, and this in turn determines the required residence time for conversion.

The period for intimate contact of absorbent and alkylene oxide is conveniently expressed as the residence time of the fat absorbent, being the time between absorption and desorption stages. The required residence time for conversion of alkylene oxide depends on a number of factors including amount and concentration of alkylene oxide and activator such as acid or the like, prevailing temperature and pressure and the like.

Typically, residence time in prior practice conventional EO units is up to 3 minutes in the $CO_2$ absorber, 1 minute in piping and a further 3 minutes in the flasher.

Preferably, the absolute residence time in the process of the invention is greater than or equal to 11 minutes, more preferably greater than or equal to 15 minutes, more preferably is in excess of 18 minutes, for example up to 60 or 120 minutes. Most preferably, residence time is in the range 18 to 67 minutes, such as 20 to 50 minutes. The residence time varies according to the process or operation from which the contaminated fluid is derived. It is therefore convenient in some cases in which the application of this invention is a retrofit, to express residence time as additional residence time representing the increase over prior practice. For example, in an absorption stage of a conventional process, additional residence time represents the increase over the minimum residence time required to absorb and desorb fluid, including conducting fat absorbent to a flasher, flashing hydrocarbons and conducting the flashed absorbent to a desorber to desorb fluid. Expressed in this way, the process of the invention preferably provides an additional residence time of greater than or equal to 4 minutes, more preferably greater than or equal to 8 minutes, more preferably in excess of 11 minutes, for example up to 53 or 113 minutes. Most preferably, additional residence time is in the range 11 to 60 minutes, such as 13 to 43 minutes.

Preferably, the process of the invention is part of a continuous process whereby residence time is conveniently expressed as total fat absorbent volume divided by total fat absorbent flow rate, and a desired residence time is provided by selecting volume or rate accordingly. Preferably, the fat absorbent is characterized by substantially uniform flow rate, more preferably substantially plug flow, thereby conferring narrow residence time distribution. By this means a desired conversion can be attained at a lower lean absorbent volume or shorter residence time than would otherwise be possible.

The temperature of the fat absorbent may be any temperature conducive to conversion of alkylene oxide. Suitably, fat absorbent temperature is in the range of from 80° C. to 140° C., more preferably 90° C. to 130° C.

Preferably, the fluid containing the contaminant level of alkylene oxide is absorbed from a recycled gas stream or a side stream thereof which is contacted with absorbent as hereinbefore defined, and a desired amount of fluid is absorbed and separated from the recycle stream or side stream thereof. The amount of fluid absorbed from the recycle or side stream determines the amount of alkylene oxide to be converted and thereby the required conditions such as residence time for fluid remediation. The absorption of fluid is typically both temperature and time dependent and is given as a measure of absorption efficiency. In the EO process, a desired volume of $CO_2$, containing an amount of $C_1$ and $C_2$ hydrocarbons, is absorbed from the recycle stream at a desired absorber temperature to achieve the required operating protocol in terms of conversion of the ethylene to EO and to ensure a desired catalyst lifetime. At a temperature of from 70° C. to 130° C. or 140° C. the $CO_2$ absorber absorbs in the region of 50% to 99.9% $CO_2$ from the feed stream to the absorber, i.e. operates at a $CO_2$ absorption efficiency of 50% to 99.9%. Preferably the $CO_2$ absorber absorbs approximately 75% to 95% of $CO_2$ from the feed stream i.e. operates at a $CO_2$ absorption efficiency of 75% to 95% at a temperature in the range 70° C. to 110° C. and the remainder is returned to the recycle stream.

We have found, however, that at this temperature the conversion of alkylene oxide according to the present invention is non-optimal, for example, less than 90%. For treatment of a $CO_2$ vent gas, if the temperature of $CO_2$ fat absorbent in the absorption stage is elevated to a temperature in the range of from 80° C. to 140° C., more preferably, 90° C. to 130° C. as hereinbefore defined, then a higher conversion in the range 90% to substantially complete conversion of the contaminant alkylene oxide may be obtained.

There is, therefore, a conflict in the optimum temperature for absorption of fluid at a desired fluid absorption efficiency, and that for conversion of alkylene oxide at a desired conversion according to the present invention, and it is therefore not appropriate to simply increase the temperature of the fluid absorption, since this reduces the absorption efficiency.

In a preferred embodiment, therefore, the invention comprises a process for remediation of a fluid as hereinbefore defined contaminated with up to 1000 ppmv of alkylene oxide comprising contacting the fluid with an aqueous absorbent at an absorption efficiency in the range 50% to 99.9% preferably 75% to 99.9% most preferably 90% to 99.9%, to yield a fat absorbent having absorbed fluid, if required, heating the fat absorbent, and maintaining for a desired residence time for conversion of alkylene oxide, wherein the process includes subsequently desorbing absorbed fluid, cooling the lean absorbent to a temperature for the required absorption efficiency and recycling to the absorption stage. Preferably, the process is for remediating a $CO_2$-rich stream and comprises absorbing at a first temperature in the range of from 60° C. to 110° C., preferably 70° C. to 110° C., and heating, if required to a second temperature in the range of from 80° C. to 140° C. for example 90° C. to 130° C. for conversion of alkylene oxide, desorbing and cooling to a first temperature as hereinbefore defined.

The fat absorbent may be heated by any desired means and is preferably heated with a heat exchanger or other heat source in a way that is energy neutral to the process as a whole. In a particularly advantageous embodiment of the invention, fat absorbent is provided as a fluid stream whereby it is conducive to heat exchange. Preferably, therefore, heating is by heat exchange with a further process stream, such as steam, lean absorbent, stripper overhead and the like or a combination thereof, more preferably by heat exchange selected from:

a fat/lean exchanger interchanging heat between hot aqueous lean absorbent from which fluid has been desorbed and fat absorbent with absorbed fluid which requires heating;

a fat absorbent/fluid exchanger interchanging heat between hot desorbed fluid and fat absorbent with absorbed fluid which requires heating.

Alternatively or additionally heating is accomplished by using an independent source such as:

steam from another process stage, in particular steam for venting (waste steam) or cooling to water (process steam); or very hot condensate such as from the EO stripper bottom (lean absorbent); or other in-process heat sources such as EO stripper overhead and the like;

and combinations thereof.

Preferably, heat exchange comprises a line-up of suitable available heat sources and cooling sources. Preferably, the total heat exchange time is adapted for the heat exchange area and exchange volumes, and is for example 1 minute to 6 minutes.

Preferably, however, heat exchange is with a fat absorbent/fluid heat exchanger such as a fat absorbent/$CO_2$ heat exchanger.

The temperature of fat absorbent leaving the heat exchanger is regulated by altering heat input to the exchanger by known means such as adjusting the flow rate of the interchange stream, such as the lean absorbent or desorbed fluid, or adjusting heat input to the interchange stream source, such as the fluid stripper or the like. Temperature regulation may be manual or automatic, for example the process may comprise a control mechanism which alters heat input to the fat absorbent in response to detecting a change in amount of alkylene oxide in the fluid, or change in volume or flow rate of absorbed fluid.

The fat absorbent stream containing absorbent, fluid, alkylene oxide conversion product and any unconverted alkylene oxide typically also contains an amount of volatile hydrocarbons such as methane, ethylene and ethane. In a preferred embodiment, the process of the invention includes flashing the fat absorbent at reduced pressure to remove volatiles before forwarding the fat absorbent to the $CO_2$ stripper for contact with stripping medium. Volatiles removal may be facilitated by adding a flashing agent and/or adding a stripping agent as known in the art. Stripping medium is selected from any suitable stripping gases such as methane, ethane, nitrogen, steam, air, $O_2$, $CO_2$ and the like.

In the case that the process of the invention is part of a process for ethylene oxide/ethylene glycol (EO/EG) production, the condensate from the stripping of the fat absorbent stream, which comprises ethylene oxide conversion product glycol, may be sent directly for glycol recovery, or combined with the condensate from the EG production and forwarded for dewatering and glycol recovery or any other treatment in a combined or separate stage, or alternatively may be sent to waste.

Preferably, the heat of the stripped fluid stream is removed before venting the fluid or forwarding for further use. Heat removal is typically by heat exchange with the fat absorbent stream as hereinbefore defined, followed by after cooling with different means, as conventional (chiller, cooler and the like).

Accordingly, the process preferably comprises regulating the flow of lean absorbent contacting the contaminated fluid, and regulating the residence time of fat absorbent, for example, by addition of inert gases and like techniques as known in the art for reduced flow rate and increased residence time, and/or comprises regulating the temperature of fat or aqueous absorbent by heat exchange or other means as hereinbefore defined.

In a further aspect of the invention, there is provided a method for calculating a required residence time of fat absorbent in a process for remediation of fluid as hereinbefore defined, from the moment of fluid absorption to the moment of fluid stripping to generate lean absorbent, in such a manner as to convert a desired amount of ethylene oxide as hereinbefore defined. Preferably, the method comprises compiling a set of kinetic data for the process in question relating to reduction in residual ethylene oxide with increasing residence time at a number of temperatures, compiling a relation as in FIG. 5 and determining an appropriate temperature and/or time for operation for a particular ethylene oxide concentration in fluid to be remediated.

In a further embodiment, the process of the invention comprises an additional end-of-pipe incineration of the fluid stream after conversion of alkylene oxide as hereinbefore defined. End-of-pipe incineration which is the current practice for remediating a $CO_2$ vent stream and is effective for combusting any levels of EO or other hydrocarbons, is not suited for full time operation, for the reasons described above. Preferably, therefore, the process provides for additional permanent, temporary or semi permanent end-of-pipe incineration. This is useful in the event of accidental release of high levels of ethylene oxide to the fluid stream, for example, in the case of process malfunction. It is also useful in the event of incidental increase of alkylene oxide levels, for example, in processes adopting minimal additional residence time to achieve initial alkylene oxide reduction or alkylene oxide reduction at usual loading levels, and requiring an additional end-of-pipe solution to complete alkylene oxide reduction or in times of higher fluid loading or higher alkylene oxide contamination.

In a further aspect of the invention, there is provided a process for the conversion of ethylene to ethylene oxide (EO) with formation of byproducts, water and $CO_2$, wherein the product EO is isolated from the recycle gas and $CO_2$ is removed from the recycle and the $CO_2$ gas stream is remediated by the process as hereinbefore defined. Preferably the process comprises in an additional stage the conversion of product EO to EG.

The amount or volume of fluid to be remediated and the concentration of alkylene oxide therein determine the amount or volume of alkylene oxide to be converted. The fluid absorption efficiency, for example, $CO_2$ absorption efficiency for absorption from the recycle stream of the EO process, and the concentration of alkylene oxide, for example in the recycle stream, determine the amount of alkylene oxide absorbed with fluid, for example $CO_2$ from the recycle stream and thereby the requirements for the process of the invention. However, it would be desirable to operate the remediation process of the invention without impacting the other stages of the process of which it forms a part.

In a particular advantage of the invention, it has been found that the process of the invention may be operated at increasing alkylene oxide levels in the contaminated fluid stream while still obtaining a remediated fluid stream having a desired maximum residual alkylene oxide level of 1 ppmv or preferably 0.1 ppmv by selection of operating conditions as hereinbefore defined.

In a preferred embodiment of the invention, there is therefore provided a process for remediation of a fluid contaminated with an amount of up to 1000 ppmv alkylene oxide, especially a $CO_2$ vent gas in an EO unit, comprising contacting fluid with aqueous absorbent to form fat absorbent comprising fluid and alkylene oxide in any volume or at any rate, and converting alkylene oxide, wherein the process comprises determining suitable conditions at any time, selected from amount or temperature of aqueous absorbent, residence time or temperature of fat absorbent or the like, to convert a desired amount of alkylene oxide and maintain at a residual alkylene oxide level less than 0.1 ppmv, and without affecting volume or rate of further fluid absorption. Preferably, the process comprises selecting an appropriate combination of fat absorbent temperature and residence time at any given moment, optionally together with incineration.

Preferably, the process for the conversion of ethylene of the invention is operated as known in the art in a multitubular fixed bed reactor, and comprises reacting gaseous ethylene and oxygen over a catalyst at a temperature in the range of 200° C. to 300° C., and at a pressure in the range of 12 bara to 25 bara.

The EO/EG process is illustrated as a block scheme in FIG. 1. In FIG. 1 and in the corresponding process sketch of FIG. 3, the conventional $CO_2$ removal is illustrated. Ethylene and water are supplied 1 to the multitubular fixed bed reactor 2 where the EO reaction takes place by the silver-catalysed oxidation of ethylene to ethylene oxide. A large gas stream flows through the reactor tubes 2, which contain the catalyst. The heat generated by the chemical reaction is removed by evaporation of coolant at the shell side of the reactor, which is used for the production of steam. The generated steam is used as heat medium in the glycol reaction and recovery sections of the plant, in the case of a combined EO/EG process.

Typically, the stream 3 exiting the reactor comprises small quantities of ethylene oxide together with large amounts of residual gases including unconverted ethylene and oxygen as well as appreciable quantities of carbon dioxide, low molecular weight hydrocarbons and inert gases such as nitrogen. Reaction products (ethylene oxide and water) are removed in the EO recovery section 4. Unconverted oxygen and ethylene are recycled back into the reactor via the recycle stream 5. In the EO recovery section 4, EO is recovered from the gaseous reactor effluent by absorption in water at a temperature in the range of from 15° C. to 30° C. (EO lean absorbent) and is processed in a variety of ways including fractionation, scrubbing and stripping at a temperature in the range of from 100° C. to 135° C. and the like. The diluted aqueous EO solution (EO fat absorbent) is concentrated in the EO stripper (part of 4, not shown) where an EO/water mixture leaves over the top and a lean absorbent from the bottom. After cooling the EO lean absorbent is returned to the EO absorber.

A slipstream of the lean absorbent (not shown) is sent to the glycols recovery section for recovery of glycols that are formed by hydration of a small fraction of the absorbed EO.

Product EO is removed as high purity EO or sent as feed to an EG reaction unit for reaction to form ethylene glycol (EG).

A small bleed stream 6 is withdrawn from the recycled gases 5 to prevent build up of impurities such as argon, ethane or nitrogen in the recycle gas loop. The bleed stream can be used as fuel gas, and preferably all or part of the bleed stream is forwarded for ethylene recovery.

A side stream 7, part or all of the recycle gas, is sent to the $CO_2$ removal section 8 in which it is scrubbed 9 with an aqueous $CO_2$ absorbent for removal of excess $CO_2$ forming a $CO_2$ fat absorbent which is subsequently flashed for light ends removal 10, $CO_2$ is stripped 11 from the absorbent and typically is vented 12, or if desired, recovered for use or sale as a by-product.

FIG. 3 illustrates this process in more detail, showing the side stream 7 conducted via a heat exchanger 90 in which it is contacted with and cools recycled hot lean carbonate 110. By this means the temperature in the $CO_2$ absorber can be regulated to determine the desired degree of uptake of $CO_2$—high levels of absorption require cooling of lean absorbent. Residual unabsorbed gases exiting from the absorber overhead 91 are cooled and conducted to gas knockout drum 92 from which the overhead gases 93 are returned to the gas loop, and to the EO reactor 2 and the bottom stream 94 comprising condensed water is combined in the stripper 10 with fat absorbent 95 from the $CO_2$ absorber.

$CO_2$ fat absorbent 95 exits from the bottom of absorber 9 and passes to flasher 10 from which volatiles 100 leave as overhead, and liquids including fat absorbent 101 leave at the bottom and enter the stripper 11. Lean absorbent 110 leaves at the bottom. Gaseous $CO_2$ and steam forms the overhead 111, and is conducted to the overhead knockout 112 from which $CO_2$ is vented 12 and condensed water 113 recycled to stripper 11 and/or sent for treatment.

Returning to FIG. 1 the recycle stream 5 containing unconverted oxygen and ethylene and other residual gases together with overhead gases from the $CO_2$ removal unit 8 are recycled back to the reactor 2. Fresh feeds are supplied in the recycle stream 1. The oxygen is thoroughly mixed with the hydrocarbon recycle gas stream in a specially designed mixing device having safeguarding mechanisms and oxygen cut off and immediate nitrogen purge for safety. A ballast gas is used to ensure a maximum allowable oxygen concentration in the recycle gas loop.

It is a particular advantage that the EO process may be minimally modified by the process of the invention. Preferably, the process is modified by increasing the volume of lean absorbent in the $CO_2$ removal section, to confer increased residence time and optionally additionally heating the fat absorbent in the $CO_2$ removal section, for example by diverting a process stream such as the $CO_2$ stripper overhead for heat exchange with the fat absorbent. Additionally, the process may include a mixing stage for mixing additional contaminated fluid streams.

The increase in volume of lean absorbent which is required depends, however, on plant size and may be determined by those skilled in the art. A typical example for a world scale year 2000 plant would require additional lean absorbent volume in the range of from 50 m³ to 350 m³, more preferably 80 m³ to 300 m³, for example 100 m³ to 150 m³, depending on the capacity of the EO process, for example 300 kT/a-400 kT/a.

The $CO_2$ removal section in a modified EO/EG process incorporating the process of the invention is illustrated as a block scheme in FIG. 2 and as a process sketch in FIG. 4.

In this case, the side stream 7, part or all of the recycle gas, is sent to the $CO_2$ removal section 8 in which it is scrubbed 9 with an aqueous $CO_2$ absorbent for removal of excess $CO_2$ as in the conventional process of FIGS. 1 and 3. In this case, however, the bottom stream 95 which comprises $CO_2$ fat absorbent is conducted to an intermediate EO converter unit 13. As in FIG. 3 the lean carbonate is cooled by $CO_2$ absorber gas feed in heat exchanger 90 for optimal $CO_2$ absorption. However, this means that fat absorbent exiting absorber 9 is at optimum absorption temperature but may not be at a temperature sufficient for EO conversion to glycol. In this case, and in a particularly advantageous manner, which is compatible with the process as a whole, the fat absorbent may be heated 120 on entry to the converter 13 and is held for a required residence time. The fat absorbent then exits the converter 13 and is subsequently flashed 10 for light ends removal 100. $CO_2$ is stripped 11 from the absorbent as in the conventional process. Steam, including entrained glycol, exits from the overhead of the stripper 11 with the $CO_2$ 111 and is conducted to a knockout drum 112, from which $CO_2$ exits as the overhead stream and as in the conventional process is vented 12, or if desired, recovered for use or sale as a by-product, and condensed water containing glycol exits from the bottom 113. The condensate stream is in its entirety or in part sent as a bleed stream for treatment.

FIG. 4 illustrates a preferred modification by which water 94 condensed from the $CO_2$ absorber overhead gas knockout 92 is combined with fat carbonate exiting the bottom of absorber 9 which in a particular advantage additionally allows treatment of any EO present in the overhead condensate 92.

FIG. 4 illustrates one way, specifically heat exchange in exchanger 120 with $CO_2$ stripper overhead 111, in which the conventional process is modified for heat exchange to heat the fat absorbent.

In fact, the process may be modified for heat exchange in any suitable manner to heat the fat absorbent, and alternative modifications are illustrated in FIG. 5. For example hot lean carbonate 110 may be used to heat fat carbonate. Alternative means make use of an independent heat source in combination with outlet/inlet fat absorbent heat exchange as hereinbefore defined. For example, steam as an independent heat source may be used to heat $CO_2$ fat absorbent stream 95 directly.

FIG. 5 also illustrates an alternative means whereby $CO_2$ absorber overhead gas knockout condensate 94 may be treated to remove alkylene oxide independently, by heating with steam to a very high temperature in excess of 130° C. up to 210° C. at which EO reacts away immediately whereby purified condensate 940 can then be used directly in flasher 10, as in the conventional process.

Preferably, the process of the invention is used in an EO process for producing EO as a commercial product, for example, selected from sterilization agents, fumigants, and the like or may be used as a starting material in the manufacture of glycols and the like for the preparation of a diversity of products such as anti-freeze, cosmetics, lubricants, plastics and surfactants.

In a further aspect of the invention, there is provided an apparatus for remediation of fluid as hereinbefore defined contaminated with up to 1000 ppmv of alkylene oxide, wherein the apparatus comprises a converter having inlet means connected to the outlet of a fluid absorber for contacting fluid and aqueous absorbent, a holding unit having a volume V for the fat absorbent, and outlet means connected to the inlet of a fluid desorber. Suitably, the volume V of the holding unit is determined having regard to the flow rate of the fat absorbent, and other factors as relevant, to confer suitable residence time for conversion of alkylene oxide as hereinbefore defined.

Preferably, the apparatus is suitable for use in the process for converting alkylene oxide comprised in a fluid as hereinbefore defined. In the case that the apparatus is suitable for remediating more than one fluid, preferably, the fluids are combined upstream of the inlet or additional inlet means are provided upstream of the holding unit or at the upstream end thereof. Preferably, the apparatus comprises means for mixing additional fluid streams, more preferably to provide substantially uniform fat absorbent composition, for example, comprises a mixing pump at the combined inlet or additional inlets.

Preferably, the volume V of the holding unit is in the range of from 50 m³ to 350 m³, and more preferably 100 m³ to 300 m³, and is selected with regard to the required volume of fat absorbent to provide the desired residence time distribution as hereinbefore defined. For the purpose of illustration, volumes are related to world scale plants as built in year 2000 with EOE (EO equivalent) capacities of 300 kT/a to 400 kT/a. Accordingly, it is within the competence of the skilled person to determine a suitable volume for apparatus in other units or in units at different volumes.

The holding unit may be of any desired shape or configuration and may have any desired internals suitable for holding the fat absorbent. Preferably, the holding unit is shaped and configured and/or provides internals whereby fluid flow through the apparatus approaches plug flow, whereby residence time distribution of the fat absorbent is substantially uniform. By this means, a desired conversion can be attained at a lower holding unit volume than would otherwise be possible.

Preferably, therefore, the holding unit comprises one or more elongate conduit means ensuring minimal back mixing and flow divergence. Conduit means has length l and diameter d providing a length to diameter ratio l/d which may be greater than or equal to 10, preferably greater than or equal to 25, more preferably in the range of from 30 to 600, more preferably in the range 40 to 500 most preferably in the range 50 to 375, or 50 to 150. Accordingly, diameter may be in the range 0.5 m to 2 m, preferably 0.75 m to 1.90 m, more preferably, approximately 0.8 m; and length may be in the range 10 m to 600 m, preferably 20 m to 500 m, more preferably, approximately 300 m or 400 m. A plurality of conduits may be provided in parallel or in series thereby providing a compact holding unit and dispensing with thermal insulation and like considerations. Preferably, one or more conduit means comprise one or more elongate pipes.

Internals which may be provided in the holding unit as hereinbefore defined are suitably selected from baffles, structured or unstructured packing and other internals known to provide flow approaching plug flow and substantially uniform residence time distribution.

Preferably packing, if present, has a high void fraction to avoid increasing the size of the holding unit while still providing the desired volume V, more preferably packing comprises a packed bed. A packed bed may have dimensions given as length/diameter greater than 2, for example having length in the range 10 m to 50 m and diameter in the range 3 m to 6 m.

A plurality of conduit means may be provided, for example, as a horizontal or vertical aligned cluster of parallel aligned conduit means adapted for distribution of the fat absorbent stream uniformly across all conduits at the inlet means and adapted for the convergence of fat absorbent at the outlet means. Distribution means may comprise guide vanes or the like or may comprise fluting portions of each conduit having an initial diameter equal to the diameter of the inlet means divided by the number of conduits and having a final diameter equal to the conduit diameter, the fluting portion being straight or curved in manner to provide fluid association of the converter inlet with the conduit in question.

Alternatively, the holding unit may comprise one or more conduits configured in a plane as a circular or square spiral or as alternate linear and 180° bent sections in the form of a repeated folding configuration or the like.

A holding unit comprising a plurality of planar configured conduits as defined is conveniently provided as a horizontal or vertical stack of planar conduits. The holding unit may have distribution and convergence means as hereinbefore defined, in the case that the holding unit comprises combined conduit diameter in excess of inlet diameter, or may simply comprise packing or stream dividers to reduce turbulence, in the case that the combined conduit diameter is substantially equal to the inlet diameter.

Preferably, the holding unit is characterized by Peclet number, Pe, in excess of 10. Suitable Pe is the range of from 10 to 10,000, for example 100 to 2500, preferably 150 to 450, although other Pe values may be envisaged which provide for conversion of alkylene oxide, but at lower efficiencies of operation, and therefore not benefiting from synergies which are of particular advantage in the present invention. Peclet number is defined, for a conduit type holding unit, as $Pe = <v> \times L/D_L$, where $<v>$ is the average fluid velocity, L the length of the tube and $D_L$ is the longitudinal (or axial) dispersion coefficient. The latter can be calculated by one of the correlations known in the art. For a packed bed, Pe can be calculated using the well known so-called Bodenstein Bo=2 relation, where $Pe = Bo \times L/d_p$ ($d_p$ being the particle diameter).

In a preferred embodiment of the invention, the apparatus comprises heating means associated with the inlet means of the holding unit, selected from heating means as known in the art. Preferably, heating means comprises a heat exchanger providing heat exchange between fat absorbent and another process stream at higher temperature as hereinbefore defined such as steam, lean absorbent, stripper overhead and the like, or a combination thereof, more preferably by heat exchange selected from:

a fat/lean exchanger interchanging heat between hot aqueous lean absorbent from which fluid has been desorbed and fat absorbent with absorbed fluid which requires heating;
  a fat absorbent/fluid exchanger interchanging heat between hot desorbed fluid and fat absorbent with absorbed fluid which requires heating.

Alternatively or additionally heating is accomplished by using an independent source such as:
  steam from another process stage, in particular steam for venting (waste steam) or cooling to water (process steam); or
  very hot condensate such as from the EO stripper bottom (lean absorbent); or
  other in-process heat sources such as EO stripper overhead and the like;
  and combinations thereof.

Preferably, heat exchange comprises a line-up of suitable available heat sources and cooling sources. Preferably, the total heat exchange time is adapted for the heat exchange area and exchange volumes, and is for example 1 to 6 minutes, with a heat exchange area of for example 750 m².

Preferably, the unit comprises a heat exchanger section wherein the fat absorbent stream is brought into thermal communication with the stripper overhead comprising hot $CO_2$, thereby heating the fat absorbent at the upstream end of the holding unit and cooling the stripper overhead $CO_2$ before venting or forwarding for other applications.

A heat exchanger may be of any type as known in the art and is suitably of the shell and tube type or plate and frame type and is suitably provided at the upstream end or as part of the inlet means of the holding unit. Fat absorbent temperature may be regulated by heat exchanger factors such as selecting heat transfer area, and materials of heat exchanger (heat exchange coefficient) also selecting the temperature of the heat donating stream and the flow rates of respective streams.

The apparatus of the invention may be part of any apparatus in which a fluid stream is produced having an amount of contaminating ethylene oxide. Preferably, the apparatus is part of an EO unit for the conversion of ethylene to EO, more preferably part of an EO/EG unit, as hereinbefore defined.

It is a particular advantage that an EO unit may be minimally modified by the apparatus of the invention. Preferably, the unit is modified by incorporating the apparatus in the feed stream to $CO_2$ vent, to confer increased residence time, optionally, additionally including a heat exchanger, for example, by diverting a stream conduit such as the $CO_2$ stripper overhead conduit for heat exchange with the fat absorbent. Additionally, the unit may include means for mixing additional contaminated fluid streams.

In a further aspect of the invention, there is provided an EO unit for the conversion of ethylene to ethylene oxide with formation of byproducts, water and $CO_2$, wherein the product EO is isolated from the recycle gas and $CO_2$ is removed from the recycle and is remediated using the apparatus as hereinbefore defined.

The invention is now illustrated in a non-limiting manner with reference to the following examples.

EXAMPLES

Comparative Example

Conventional Process without Treatment of EO in the Feed Stream for $CO_2$ Removal The process of the operation as shown in FIGS. 1 and 3 makes use of a multitubular fixed bed reactor to produce ethylene oxide, and comprises contacting gaseous ethylene and oxygen with a silver on alumina catalyst (CRI EO catalyst S882) at a temperature in the range of 200 to 300° C., and at a pressure in the range of 12 to 22 bara.

Unconverted oxygen and ethylene are recycled back into the reactor via the recycle stream. Reaction products (ethylene oxide and water) are removed in the EO recovery and removal section and fresh feeds are supplied.

A small bleed stream is withdrawn from the recycle gas and vented. The process results in gas leaving the EO reactor which carries an undesirable by-product $CO_2$, which has to be removed to avoid excessive build up that may impede EO production.

A $CO_2$ removal section, therefore, provides for an amount of $CO_2$ to be removed from the recycle and vented. A feed stream to the $CO_2$ removal section is contacted with an aqueous carbonate absorbent solution which selectively absorbs $CO_2$ from the recycle stream and which contains potassium carbonate, potassium bicarbonate with potassium vanadate and potassium borate as activators. The fat absorbent is then flashed and stripped to remove volatiles and yield $CO_2$ which is suitable for venting.

The feed stream for $CO_2$ removal can contain EO of the order of up to 500 ppm volume or even higher if not treated properly. In this example, the EO concentration in this stream is 32 ppmv. Conditions and results are shown in Table 1.

Example 1

Process of the Invention with Increased Residence Time

In the process of the invention, the $CO_2$ removal unit is modified by incorporating an EO Converter of the invention comprising a reactor with substantially plug flow characteristics and a volume of 255 m$^3$, as shown in FIGS. 2 and 4, resulting in an additional residence time of about 23.75 minutes. The plug flow reactor is provided as a 0.8 m diameter pipe of length 300 m, and has a sufficient high maximum allowable operating pressure of about 2200 kpa. In operating the apparatus, an additional volume of the activated carbonate solution, as lean absorbent solution, of an amount of 225 m$^3$ is incorporated. The fat absorbent has a pH of from 10.2 to 10.5.

In this example, the condensed water from the $CO_2$ absorber overhead gas knockout is added to the fat absorbent as shown in FIG. 4.

In the EO Converter the absorbed EO is converted to glycol and is removed from the $CO_2$ removal unit with the condensed water from the $CO_2$ absorber overhead (113) and is sent to waste water with the existing stream, as shown in FIGS. 4 and 5.

Operation of the process and the apparatus of the invention guarantees sufficient conversion of absorbed EO in the $CO_2$ removal unit to reach less than about 0.001 kg/hr EO in the $CO_2$ vent.

Conditions and results of Example 1 are shown in Table 1.

Example 2

Process of the Invention with Increased Residence Time and Heating of Fat Carbonate Operating the $CO_2$ removal unit under the conditions as described in Example 1 results in unfavorable $CO_2$ absorption conditions. To reach high absorption efficiency the temperature in the $CO_2$ absorber has to be lowered to a level as mentioned in the first column of Table 1. That, however, would result in much lower EO conversions in the EO converter: with the apparatus of above Example 1 and under the same flow and same residence times, that would result in an amount of EO in the $CO_2$ vent in excess of 0.1 kg/h.

In order to reach the required conversion in the $CO_2$ removal unit the temperature of the fat carbonate has to be increased. This is preferably done in a way that is energy neutral to the process. Amongst others, two options are available: (1) a fat/lean heat exchanger interchanging heat between fat and lean carbonate or (2) a fat carbonate/$CO_2$ heat exchanger interchanging heat between $CO_2$ stripper overhead and the fat carbonate. Other methods can use (waste) steam heat or very hot condensate as independent heat source with or without outlet/inlet heat integration.

In this Example again the condensed water from the $CO_2$ absorber overhead gas is added to the fat absorbent as shown in FIG. 4.

The surface area for a fat carbonate/$CO_2$ heat exchanger was 750 m$^2$. With this heat exchanger, the fat carbonate temperature was increased to 92(91)° C. without substantially changing conditions elsewhere in the process. The fat carbonate has a residence time in the piping and carbonate flasher of about 10 minutes as well as up to about 1 or 2 minutes in the new fat carbonate/$CO_2$ heat exchanger. In order to achieve the required EO conversion, additional residence time was provided in the new EO Converter, as described in Example 1.

The conversion of absorbed EO in the $CO_2$ removal unit was found to give less than about 0.001 kg/hr EO in the $CO_2$ vent, as in Example 1. This is despite lowering the temperature in the $CO_2$ absorber. The result, with a combination of increased temperature and residence time, gives both excellent $CO_2$ absorption and excellent EO conversion.

Conditions and results of Example 2 are shown in Table 1.

TABLE 1

EO in vent gas under several different process conditions

| Process value (avg. daily data) | Comparison | Ex 1 | | Example 2 | |
|---|---|---|---|---|---|
| Lean carbonate to $CO_2$ absorber t/d | 11320 | 17326 | 17326 | 13079 | 13216 |
| Recycle gas to $CO_2$ absorber t/d | 7259 | 5275 | 5275 | 8487 | 8507 |
| EO content in gas feed to absorber/kg/h | 225 | 14 | 14 | 101 | 157 |
| Bottom temperature $CO_2$ absorber/° C. | 78 | 94.5 | 94.5 | 74.8 | 75 |
| Residence time fat absorbent in $CO_2$ absorber/min | 4 | 3 | 3 | 3.5 | 3.5 |
| Residence time piping bottom $CO_2$ absorber to heater/min | 3 | 2 | 2 | 2.5 | 2.5 |
| Temperature outlet heater/° C. | — | — | — | 90.6 | 89.7 |
| Residence time EO Converter/min | — | — | 23.75 | 31.5 | 31.3 |
| Temperature outlet EO Converter/° C. | — | — | — | 90.7 | 89.9 |
| Temperature rich carbonate flasher/° C. | 78 | 94.5 | 94.5 | 90.7 | 89.9 |
| Stripping gas feed to carbonate flasher/t/d | 7.5 | 12.9 | 12.9 | 11.5 | 11.5 |
| Residence time in flasher/sec | 281 | 177 | 177 | 234 | 232 |

TABLE 1-continued

EO in vent gas under several different process conditions

| Process value (avg. daily data) | Comparison | | Ex 1 | Example 2 | |
|---|---|---|---|---|---|
| $CO_2$ vent gas stream to ventstack/kg/h | 12218 | 9497 | 9497 | 8717 | 3213* |
| EO concentration in vent stream/ppmv | 293 | 38 | <0.1 (calc.) | <0.1 | <0.1 |

*remainder was collected for sale as a commercial product

FIG. 6 illustrates typical residual EO against residence time for conversion at a range of temperatures.

Example 3

Apparatus of the Invention—Design of EO Converter (Holding Unit)

The design of an EO Converter was optimized to develop different configurations suitable for different reactors and operating conditions. The results are shown in Table 2.

TABLE 2

EO Converter configurations according to the invention with equivalent EO conversion of 99.92% for all cases.

| | Diameter | Length | Volume | Pe | |
|---|---|---|---|---|---|
| 50 parallel pipes | 0.5 m | 28 m | 276 m³ | 101 | |
| 1 pipe | 0.5 m | 1314 m | 258 m³ | 10001 | |
| 1 pipe | 0.8 m | 515 m | 259 m³ | 2311 | |
| 1 pipe | 1.2 m | 230 m | 260 m³ | 653 | |
| 1 pipe | 2 m | 86 m | 271 m³ | 138 | |
| Packed bed | 4 m | 22 m | 300 m³ | 133 | Void fraction 0.9, particle size 2 cm |
| Packed bed | 5 m | 16 m | 310 m³ | 88 | Void fraction 0.9, particle size 2 cm |

Alternative holding unit dimensions having Pe less than 450 include Pe=419 or 208, a diameter of 0.8 m or 11.0 m and length is 300 m or 400 m.

A single pipe is engineered into a "vessel" reactor by folding the pipe. The "vessel" reactor is illustrated in FIG. 7. The depth of the channels are equal to the width and do not exceed 2 meters. Several of the slices as drawn in the Figure are stacked on top of each other with the outlet of each slice connected to the inlet of the following one, such that all channels are connected in series. There is no preference for the channels running in horizontal or vertical direction.

A variant "vessel" reactor is a cylindrical vessel packed with cylindrical pipes which are connected in series by 180° bends in similar manner to FIG. 7.

What is claimed is:

1. An apparatus for production of a $CO_2$ gas stream containing no more than 1 ppmv of alkylene oxide contaminant from a $CO_2$-rich stream contaminated with alkylene oxide wherein the apparatus comprises:
  a converter comprising:
    an inlet means connected to an outlet means of a fluid absorber, said inlet means for receiving from said fluid absorber a fat absorbent containing $CO_2$ and up to 1000 ppmv of alkylene oxide contaminant, said absorbent having removed said $CO_2$ and alkylene oxide contaminant from said $CO_2$-rich stream; and
    a holding unit configured to provide flow approaching plug flow and to provide substantially uniform residence time distribution and having a volume V which is sufficient to provide suitable residence time for sufficient conversion of the alkylene oxide contaminant in the fat absorbent to alkylene glycol such that no more than 1 ppmv of alkylene oxide contaminant is present in said $CO_2$ gas stream, and
    an outlet means; and
  a $CO_2$ desorber for separating said $CO_2$ gas stream containing no more than 1 ppmv of alkylene oxide contaminant from said fat absorbent and said alkylene glycol, said desorber having an inlet means connected to the outlet means of said converter.

2. The apparatus of claim 1 wherein the holding unit comprises one or more elongate conduit means for ensuring minimal back mixing and flow divergence.

3. The apparatus of claim 1 wherein the holding unit comprises internals adapted to provide flow approaching plug flow and to provide substantially uniform residence time distribution.

4. The apparatus of claim 1 wherein the holding unit is characterized by a Peclet number greater than 10.

5. The apparatus of claim 1 which comprises heating means associated with the inlet means of the holding unit.

6. The apparatus of claim 1 wherein the fluid absorber fluidly communicates with a unit for the conversion of ethylene to ethylene oxide.

7. The apparatus of claim 1 wherein the desorber is a volatiles flasher or a $CO_2$ stripper.

8. A process for reduction of alkylene oxide contaminant in a $CO_2$ vent stream to no more than 1 ppmv, the process comprising:
  oxidizing alkylene to produce residual gas comprising product alkylene oxide;
  isolating product alkylene oxide from the residual gas, producing $CO_2$-rich recycle gas comprising contaminant alkylene oxide;
  contacting at least a portion of the $CO_2$-rich recycle gas with lean $CO_2$ absorbent, said contacting occurring under absorption conditions effective to produce fat $CO_2$ absorbent comprising containing $CO_2$ and up to 1000 ppmv of contaminant alkylene oxide;
  subjecting at least a portion of the fat $CO_2$ absorbent to conversion conditions effective to convert contaminant alkylene oxide to glycol, thereby producing a remediated $CO_2$-containing fluid; and
  subsequently subjecting at least a portion of the remediated $CO_2$-containing fluid to conditions effective to desorb the $CO_2$, producing a remediated $CO_2$ vent stream which contains no more than 1 ppmv alkylene oxide.

9. The process of claim 8 comprising contacting the $CO_2$-rich recycle gas with a volume of lean $CO_2$ absorbent greater than required to absorb the total $CO_2$ amount of in the $CO_2$-rich recycle gas.

10. The process of claim 8 wherein the alkylene oxide is ethylene oxide.

11. The process of claim 9 wherein the alkylene oxide is ethylene oxide.

12. The process of claim 8 further comprising providing lean $CO_2$ absorbent selected from the group consisting of alkaline metal carbonates, water, methyl alcohol, acetone, propylene carbonates, ethylene carbonates and mixtures thereof, optionally combined with a component selected from the group consisting of another absorbent, activator, and a combination thereof.

13. The process of claim 8 wherein said absorption conditions comprise a total residence time of eleven minutes or more.

14. The process of claim 8 wherein said conversion conditions comprise a contaminated fat $CO_2$ absorbent temperature of from 80° C. to 140° C.

15. The process of claim 14 wherein the contaminated fat $CO_2$ absorbent temperature is provided by heat exchange with a different process stream.

16. The process of claim 15 wherein said conversion conditions comprise a contaminated fat $CO_2$ absorbent temperature of from 90° C. to 130° C.

17. The process of claim 8 further comprising:
separating the glycol from the remediated $CO_2$-containing fluid to produce remediated lean $CO_2$ absorbent which is substantially free of alkylene oxide; and,
recycling the remediated lean $CO_2$ absorbent for contacting the $CO_2$-rich recycle gas.

18. A remediated $CO_2$ vent stream prepared by a process comprising:
oxidizing alkylene to produce residual gas comprising product alkylene oxide;
isolating product alkylene oxide from the residual gas, producing $CO_2$-rich recycle gas comprising contaminant alkylene oxide;
contacting at least a portion of the $CO_2$-rich recycle gas with lean $CO_2$ absorbent, said contacting occurring under absorption conditions effective to produce fat $CO_2$ absorbent comprising containing $CO_2$ and up to 1000 ppmv of contaminant alkylene oxide;
subjecting at least a portion of the fat $CO_2$ absorbent to conversion conditions effective to convert sufficient contaminant alkylene oxide to glycol to achieve the desired amount of alkylene oxide contaminant in said $CO_2$ vent stream, thereby producing a remediated $CO_2$-containing; and
subsequently subjecting at least a portion of the remediated $CO_2$-containing fluid to conditions effective to desorb the $CO_2$, producing a remediated $CO_2$ vent stream which contains no more than 1 ppmv alkylene oxide.

19. The vent stream of claim 18 wherein the remediated $CO_2$ vent stream contains 0.1 ppmv or less of alkylene oxide.

20. A remediated lean $CO_2$ absorbent prepared by a process comprising:
oxidizing alkylene to produce residual gas comprising product alkylene oxide;
isolating product alkylene oxide from the residual gas, producing $CO_2$-rich recycle gas comprising contaminant alkylene oxide;
contacting at least a portion of the $CO_2$-rich recycle gas with lean $CO_2$ absorbent, said contacting occurring under absorption conditions effective to produce fat $CO_2$ absorbent comprising containing $CO_2$ and up to 1000 ppmv of contaminant alkylene oxide;
subjecting at least a portion of the fat $CO_2$ absorbent to conversion conditions effective to convert the contaminant alkylene oxide to glycol;
separating the $CO_2$ and glycol from the fat absorbent, producing a remediated lean $CO_2$ absorbent containing no more than 1 ppmv residual alkylene oxide.

21. The absorbent of claim 20 wherein the remediated lean $CO_2$ absorbent contains no more than 0.1 ppmv residual alkylene oxide.

* * * * *